(12) United States Patent
Soskic et al.

(10) Patent No.: US 10,866,235 B2
(45) Date of Patent: Dec. 15, 2020

(54) METHODS FOR BINDING BIOLOGICALLY ACTIVE MOLECULES TO SURFACES

(71) Applicants: Vukic Soskic, Mainz (DE); Robert Poppe, Mainz (DE)

(72) Inventors: Vukic Soskic, Mainz (DE); Robert Poppe, Mainz (DE)

(*) Notice: Subject to any disclaimer, the term of this patent is extended or adjusted under 35 U.S.C. 154(b) by 374 days.

(21) Appl. No.: 15/500,732

(22) PCT Filed: Jul. 30, 2015

(86) PCT No.: PCT/EP2015/067523
§ 371 (c)(1),
(2) Date: Jan. 31, 2017

(87) PCT Pub. No.: WO2016/016377
PCT Pub. Date: Feb. 4, 2016

(65) Prior Publication Data
US 2017/0234862 A1      Aug. 17, 2017

(30) Foreign Application Priority Data
Aug. 1, 2014  (DE) .................. 10 2014 215 208

(51) Int. Cl.
*G01N 33/543*      (2006.01)

(52) U.S. Cl.
CPC ..... *G01N 33/54353* (2013.01); *G01N 33/543* (2013.01); *G01N 33/54366* (2013.01)

(58) Field of Classification Search
CPC ........... G01N 33/54353; G01N 33/543; G01N 33/54366
See application file for complete search history.

(56) References Cited

U.S. PATENT DOCUMENTS

2014/0046027 A1* 2/2014 Laine ............... C08B 15/06
530/363

FOREIGN PATENT DOCUMENTS

WO    WO-2012120198 A1 *  9/2012 ............. C08B 15/06

OTHER PUBLICATIONS

Dirks et al. Monitoring protein-polymer conjugation by a fluorogenic Cu(I)-catalyzed azide-alkyne 1,3-dipolar cycloaddition. Bioconjugate Chem. 2009, vol. 20, pp. 1129-1138. (Year: 2009).*
Huang et al. Composite surface for blocking bacterial adsorption on protein chips. Biotechnology & Bioengineering, 2003, vol. 81, No. 5, pp. 618-624. (Year: 2003).*
Heyes et al. Biocompatible surfaces for specific tethering of individual protein molecules. J. Phys. Chem. B. 2004, vol. 108, pp. 13387-13394. (Year: 2004).*
Lin et al. Analyzing DNA-protein interaction on a chip. Integrated biochips for DNA analysis 2007, pp. 1-201, Published by Landes Nioscience, 1002 West Avenue, Austin, Texax 78701, USA. (Year: 2007).*
Wangkam et al. Adsorption of bovine serum albumin (BSA) on polystyrene (PS) and its acid copolymer. Current Applied Physics 2012, vol. 12, pp. 44-52. (Year: 2012).*
Sun Xue-Long et al: "Carbohydrate and protein immobilization onto solid surfaces by sequential Diels-Alder and azide-alkyne cycloadditions", Bioconjugate Chemistry, ACS, Washington, DC, US, vol. 17, No. 1, Jan. 18, 2006 (Jan. 18, 2006), pp. 52-57, XP002588543, ISSN: 1043-1802, DOI: 10.1021/BC0502311 [retrieved on Dec. 21, 2005] abstract.
Prim Denis et al: "ADIBO-based "click" chemistry for diagnostic peptide micro-array fabrication: physicochemical and assay characteristics.", Molecules (Basel, Switzerland) 2013, vol. 18, No. 8, 2013, pp. 9833-9849, XP9186176, ISSN: 1420-3049 abstract.
International Search Report cited in International Application No. PCT/EP2015/067523 dated Oct. 2, 2015, 2 pages.

* cited by examiner

*Primary Examiner* — Shafiqul Haq
(74) *Attorney, Agent, or Firm* — Rothwell, Figg, Ernst & Manbeck, P.C.

(57) ABSTRACT

The invention relates to methods for binding biologically active molecules to surfaces by coating the surface with a supported reagent in a first step and then covalently coupling said biologically active molecules to the supported reagent using a biorthogonal cycloaddition reaction. Fields of application of the invention include biochemical research, medical diagnostics and the pharmaceutical industry.

6 Claims, 4 Drawing Sheets

METHODS FOR BINDING BIOLOGICALLY ACTIVE MOLECULES TO SURFACES

CROSS REFERENCE TO RELATED APPLICATION

This application is a 35 U.S.C. 371 National Phase Entry Application from PCT/EP2015/067523, filed Jul. 30, 2015, which claims the benefit of German Patent Application No. 10 2014 215 208.9 filed on Aug. 1, 2014, the disclosures of which are incorporated by reference in their entirety.

FIELD OF THE INVENTION

The present invention relates to methods for binding biologically active molecules to surfaces by coating the surface with a carrier reagent in a first step and then covalently coupling the biologically active molecules that are to be bound to the carrier reagent by a biorthogonal cycloaddition reaction.

BACKGROUND

Many medical and pharmaceutical binding assays are based on the principle of a solid-phase immunoassay. A biologically active molecule, frequently a protein, is thereby bound to a solid carrier surface, for example to plastics particles or to the inside wall of reaction vessels such as the wells of a microplate. Binding conventionally takes place by adsorption on the surface. Such direct adsorption is a very simple binding method, but its efficiency is very variable for different molecules that are to be coated. In addition, proteins are easily denatured upon adsorption on a hydrophobic surface and thus lose biological activity. In the case of low molecular weight substances, on the other hand, there is the problem that they are bound only insufficiently by simple adsorption on the surface. In addition, there is the problem that low molecular weight substances in particular are no longer able to interact with a binding partner that is to be analysed when they are coated directly on a surface. In order to circumvent these limitations, molecules are frequently applied in biotin-modified form to surfaces which are precoated with a biotin binding protein, for example streptavidin. However, this method too has numerous limitations. In the streptavidin molecule, the binding capacity for biotinylated molecules is limited to a maximum of 4 valences per streptavidin tetramer, so that the loading density of the surface is reduced. Furthermore, streptavidin is partially denatured as well as sterically limited by the generally passive hydrophobic adsorption on the surface, so that the binding capacity for biotin-modified molecules is reduced further. Moreover, surfaces precoated with avidin or streptavidin are susceptible to non-specific interference reactions, for example by immunological cross-reactions with streptavidin or by the binding of biotin-containing molecules from the sample that is to be analysed.

U.S. Pat. No. 5,279,955 (Pegg et al.) describes heterofunctional cross-linking reagents which adsorb on plastics surfaces via a hydrophobic hydrocarbon chain and covalently bind the molecules to be coated via a cross-linking hydroxysuccinimide function. However, this method has the disadvantage that the low molecular weight carrier reagent is able to be detached from the plastics surface by detergent-containing buffers.

U.S. Pat. No. 6,713,272 (Anderson et al.) describes a method for binding biomolecules to hydrophobic surfaces based on a recombinant protein which binds with a lipid-modified domain to hydrophobic surfaces and is able to fix a ligand molecule to the surface via a second functional binding domain. A considerable disadvantage of this method is the non-covalent binding of the ligands. Furthermore, the method can be transferred to many different ligands only with considerable outlay.

U.S. Pat. No. 6,270,983 (Strohner et al.) describes the coating of surfaces with biotinylated molecules by precoating the surface with a biotinylated carrier reagent and an avidin or streptavidin layer applied thereto. However, because of the use of avidin or streptavidin layers for binding biotinylated ligands to surfaces, the problem of non-specific interferences and limited loading density remains.

Cannale et al. (Biomacromolecules. 2011, 12, 3692-3697) developed a method for coating microplates which is based on a 1,3-dipolar cycloaddition reaction between azides and sterically constrained cyclic alkynes. This method takes place under aggressive chemical conditions and is limited to the coating of synthetic peptides.

The methods hitherto known for coating surfaces with molecules have numerous limitations as regards a high loading density, the maintenance of biological activity and simple transferability of the coating method to different molecules. These limitations and disadvantages are eliminated by the present invention. In addition, there is a continuing need for methods for efficiently coating surfaces with biologically active molecules.

DESCRIPTION

The present invention relates to methods for binding biologically active molecules to surfaces by coating the surface with a carrier reagent in a first step and then covalently coupling the biologically active molecules that are to be bound to the carrier reagent by a biorthogonal cycloaddition reaction. Fields of application of the invention are biochemical research, medical diagnostics and the pharmaceutical industry.

By means of the present invention, the limitations that exist in the prior art in the binding of molecules to surfaces in relation to protein denaturing, steric blocking, non-specific interference reactions and low binding density are overcome. In addition, a simple uniform method for the stable and specific binding of different molecules to different surfaces is provided. The present invention allows surfaces to be coated with molecules in biologically active form for biochemical research and for use in diagnostic test systems.

In a first aspect, the present invention provides a method for binding biologically active molecules to a surface of a substrate, comprising the steps of:
(i) providing a carrier molecule comprising at least one click functional group,
(ii) binding the carrier molecule to a surface of a substrate, and
(iii) binding a biologically active molecule comprising at least one click functional group that is reactive towards the click functional group of the carrier molecule by cycloaddition reaction between the mutually reactive click functional groups.

By means of the method according to the invention it is possible to bind biologically active molecules to the surface of any desired solid substrate. Binding thereby takes place via a carrier molecule.

In step (i) of the method according to the invention, a carrier molecule which comprises at least one click functional group is provided. According to the invention, a "carrier molecule" is understood as being a molecule which on the one hand is capable of binding to a surface of a solid substrate and on the other hand has at least one click functional group. The carrier molecule preferably comprises a macromolecule selected from polypeptides, proteins, glycoproteins and carbohydrates. The molecular weight of the carrier molecule is preferably ≥10 kDa. The carrier molecule particularly preferably comprises human serum albumin or bovine serum albumin.

A "click functional group" within the meaning of the present invention refers to a functional group which can be made to react with a further click functional group in a cycloaddition reaction. The cycloaddition reaction between click functional groups is also referred to in the following as a click reaction.

In a first embodiment, a carrier molecule according to the invention can comprise a click functional group which is a click functional unsaturated group. Examples are dipolarophiles, such as alkenes and alkynes, as well as molecules which comprise related heteroatom functional groups, for example carbonyls and nitriles. Particularly preferred examples of click-reactive unsaturated groups are alkynes.

In a further embodiment, a carrier molecule within the meaning of the invention can comprise a click functional dipolar group. According to the invention, click functional dipolar groups are understood as being those compounds which comprise one or more heteroatoms and which have at least one mesomeric structure which represents a charged dipole. Preferred click functional dipolar groups are linear 1,3-dipolar groups, for example azide, nitrile oxide, diazoalkane, nitrilimine and nitrone.

Other click functional groups which can be used as reactants for click functional unsaturated groups are dienes such as tetrazine and tetrazole. Accordingly, a carrier molecule within the meaning of the present invention can comprise a click functional diene group, in particular tetrazine or tetrazole.

In step (ii) of the method according to the invention, the carrier molecule is bound to a surface of a substrate. Binding can take place adsorptively or covalently. Depending on the surface to be coated, suitable carrier molecules which are capable of adsorptive binding can be chosen. Alternatively, covalent binding can take place, for example via functional groups on the surface of the substrate and on the carrier molecule. Methods for covalent binding are known to a person skilled in the art.

In step (iii), a biologically active molecule is bound via the click functional group of the carrier molecule, the biologically active molecule having at least one click functional group that is reactive towards the click functional group of the carrier molecule. The reaction in step (iii) includes, for example, an incubation under suitable conditions.

The click functional groups of the carrier molecule and of the biologically active molecule are chosen such that they can be reacted with one another as reactants in a cycloaddition reaction. By means of the cycloaddition reaction, a cyclic, for example heterocyclic, linkage between the biologically active molecule and the carrier molecule already bound to the surface of a substrate is made.

A "biologically active molecule" within the meaning of the invention in principle refers to any biologically active molecule. Examples of biologically active molecules are proteins, enzymes, antibodies and nucleic acids as well as ligands of these molecules.

"Ligands" refers to any molecules which are capable of binding to a target molecule, for example to a protein, a receptor, an enzyme, an antibody or a nucleic acid. The binding of the ligand is usually reversible and is made possible, for example, by ionic bonds, hydrogen bonds, Van-der-Waals forces and hydrophobic effects.

By means of the method according to the invention it is possible in particular to bind low molecular weight biologically active molecules in such a manner that they are present in a form accessible for reactants and retain their biological activity. In a particularly preferred embodiment, a biologically active molecule within the meaning of the invention is a low molecular weight compound, in particular a low molecular weight ligand of one of the above-mentioned molecules. "Low molecular weight" within the meaning of the invention is understood as meaning a molecule having a molecular weight of <800 g/mol.

Biologically active molecules within the meaning of the invention can be, for example, natural and non-natural amino acids and oligomers or polymers thereof, for example peptides, rotaxanes, glycopeptides, proteins, enzymes, antibodies, etc. Other examples of biologically active molecules are nucleic acids and nucleic acid-analogous molecule, for example DNA, RNA, LNA, PNA, MeO-RNA, phosphorothioate nucleic acids, etc.

In a first embodiment, a biologically active molecule according to the invention can comprise a click functional group which is a dipolar group or a diene group, as defined hereinbefore in connection with click functional groups on carrier molecules. Such biologically active molecules can be bound in the method according to the invention in particular to carrier molecules that comprise a click functional unsaturated group.

In a further embodiment, a biologically active molecule within the meaning of the invention can comprise a click functional group which is an unsaturated group, as defined hereinbefore in connection with click functional groups on carrier molecules. Such biologically active molecules are suitable in particular for binding to carrier molecules which themselves comprise a click functional dipolar group or a click functional diene group.

The click functional group can be bound to the carrier molecule or to the biologically active molecule directly or via a linker. A linker within the meaning of the invention can have a chain length of approximately from 1 to 20 or more atoms. It can be flexible, for example an alkylene-based linker which may optionally comprise heteroatoms such as O, S and/or N, or it can be rigid at least in part, for example a linker which comprises at least one rigid group which can be selected from alkylene groups, alkyne groups, cyclic groups, in particular aromatic or heteroaromatic groups, but also cycloaliphatic groups and combinations thereof.

The form of the substrate can be chosen as desired according to the invention. For example, it can be in particulate form, for example in the form of microparticles or nanoparticles. Alternatively, the substrate can be in the form of a plate, in particular a microplate. The material of the substrate is in principle not limited. For example, the substrate can comprise plastics material, in particular polystyrene, polypropylene, polyethylene, polyamide, polymethacrylate, polycarbonate, polyacrylate or copolymers of polystyrene, glass, ceramics, latex, metal, in particular gold, and/or carbon.

If covalent binding of the carrier molecule to a surface of the substrate is desired, the substrate can optionally be modified prior to use in the method according to the invention so that the surface has reactive functional groups which can be reacted with functional groups of the carrier molecule to form a covalent bond.

The cycloaddition reaction in step (iii) of the method according to the invention can be carried out in principle under any reaction conditions that are suitable for the coupling of click functional groups. The cycloaddition reaction is preferably carried out in the presence of a catalyst. Methods of carrying out cycloaddition reactions between click functional groups as well as suitable reaction conditions and catalysts are known in the art.

By means of the cycloaddition reaction between the click functional groups there is preferably formed a five- or six-membered carbocycle or heterocycle. If, for example, an alkyne group and an azide group as click functional groups are reacted, the cycloaddition reaction results in the formation of a 1,2,3-triazole group as a five-membered heterocycle. The cycloaddition reaction preferably includes a (3+2) 1,3-dipolar cycloaddition with formation of a five-membered heterocycle.

The present invention relates in a further aspect to an article comprising
(i) a substrate having a surface, and
(ii) a carrier molecule,
wherein the carrier molecule is adsorptively or covalently bound to the surface of the substrate and comprises at least one click functional group.

Substrate, carrier molecule and click functional group are as defined hereinbefore.

Such a substrate precoated with click functionalised carrier molecules can be used, for example, to bind further biomolecules, as required, by click reaction.

The present invention further provides an article comprising
(i) a substrate having a surface,
(ii) a carrier molecule, and
(iii) a biologically active molecule,
wherein the carrier molecule is adsorptively or covalently bound to the surface of the substrate, and the biologically active molecule is bound to the carrier molecule via a linker which contains a group formed by click reaction.

Substrate, carrier molecule and biologically active molecule are as defined hereinbefore.

In the article according to the invention, the biologically active molecule is bound to the carrier molecule via a linker which contains a group formed by click reaction. A group formed by click reaction is understood as being a group that has been formed or is obtainable by cycloaddition between complementary click functional groups. That group is a cyclic, for example heterocyclic, group such as a 1,2,3-triazole ring.

In the articles according to the invention, the carrier molecule adsorptively or covalently bound to the substrate surface can be either cross-linked or not cross-linked. Mutually cross-linked carrier molecules form covalent bonds to adjacent, further carrier molecules.

The present invention further provides a kit comprising
(i) a substrate having a surface,
(ii) a carrier molecule which is adsorptively or covalently bound to the surface of the substrate and has at least one click functional group, and
(iii) a reagent which allows a biologically active molecule to be modified with a click functional group which is reactive towards the click functional group of the carrier molecule (ii).

In a kit according to the invention, substrate, carrier molecule and biologically active molecule are as defined hereinbefore.

The reagent (iii) for modifying a biologically active molecule with a click functional group comprises a click functional group which may optionally be present in protected form. According to the present invention, the term "reagent" can here also be understood as meaning a combination of reagents, where a combination of a plurality of reagents is required or advantageous for the modification of a biologically active molecule. Methods and reagents for modifying biologically active molecules with a click functional group are known in the art.

A further aspect of the invention relates to the use of a carrier molecule which comprises at least one click functional group and a macromolecule selected from polypeptides, proteins, glycoproteins and carbohydrates and which has a molecular weight of 10 kDa 0 kDa for the production of an article according to the invention, as defined hereinbefore. Human serum albumin and bovine serum albumin are particularly preferred as the macromolecule.

A further aspect of the invention relates to the use of an article according to the invention for determining an analyte in a sample. The determination can include a qualitative detection, for example the determination of the presence or absence of an analyte in a sample that is to be analysed. However, the invention also permits a quantitative detection of an analyte in a sample that is to be analysed. For a qualitative and/or quantitative detection, reporter groups can be determined. Such reporter groups and methods for the detection thereof are known in the art.

The analyte to be determined can be, for example, an analyte present in a biological sample, for example a biomolecule, medicament or toxic compounds. Examples of biomolecules as analytes are nucleic acids, peptides, polypeptides, saccharides, lipids, steroids, etc. For example, the analyte can be selected from nucleic acids and nucleoside-, nucleotide- or nucleic acid-binding molecules, for example nucleoside, nucleotide or nucleotide-binding proteins.

Further preferably, the analyte is a nucleic acid which can be detected by means of methods known in the art, for example hybridisation techniques. Furthermore, using an article according to the invention, an individual analyte in a sample can be detected or a plurality of different analytes can be detected in parallel. In such an embodiment, an article according to the invention preferably comprises a plurality of different biologically active molecules. These can be bound via different linkers to the carrier molecules immobilised on the substrate surface. Such different linkers comprise, for example, different cyclic groups which are obtainable by click reaction.

The sample in which an analyte is to be detected using an article according to the invention can be a biological sample, for example an agricultural sample, or a clinical sample such as a tissue sample or a sample of bodily fluid, for example blood, serum, plasma, etc. Further types of sample are inter alia soil samples, food samples, forensic samples or material samples which are to be tested for trademark protection.

The present invention will be described in greater detail below by means of the following examples and drawings.

Example 1: Production of Dibenzylcyclooctyne-PEG5-Modified Bovine Serum Albumin as Carrier Reagent The following example describes the production of dibenzylcyclooctyne-PEG5 (DBCO)-modified bovine serum albumin (BSA) as a reactive carrier reagent for the coating of surfaces. Dibenzylcyclooctyne-PEG5 N-hydroxysuccinimide was prepared by a known method (Ning, X. H. et al. (2008), Angew. Chemie-Int., 47: 2253-2255). Bovine serum albumin is dissolved in 50 mM HEPES (2-(4-(2-hydroxyethyl)-1-piperazinyl)-ethanesulfonic acid), pH 8.0, 150 mM NaCl and reacted at 22° C. for 60 minutes with a 30-times molar excess of dibenzylcyclooctyne-PEG5 N-hydroxysuccinimide. Excess reagent and low molecular weight reaction products were removed by repeated dialysis against 50 mM HEPES, pH 8.0, 150 mM NaCl. The reaction product, referred to as DBCO-BSA, was stored frozen at −20° C. until use.

Example 2: Production of Microplates Coated with DBCO-BSA Carrier Reagent

The following example describes the production of microplates (MTP) coated with DBCO-BSA as a preactivated surface for the subsequent covalent coupling of biologically active molecules by biorthogonal cycloaddition.

The carrier reagent DBCO-BSA produced according to 1.1 was diluted in a concentration of 5 μg/ml in 150 mM NaCl, 100 mM TrisHCl, pH 8.0 and pipetted in 100 μl aliquots into the wells of a microplate (Costar, Maxisorb). After incubation for 16 hours at 4° C., the wells were emptied and filled with 100 μl/well of a 1×PBS, 0.5% BSA, 0.5% sucrose solution and blocked for 1 hour at room temperature. The plates were then emptied and dried for 2 hours at 37° C. The dried plates with a DBCO-BSA carrier reagent coating were stored at 4° C. in the presence of a silica gel desiccant until further use.

Example 3: Production of Nanoparticles Coated with DBCO-BSA Carrier Reagent

The following example describes the production of paramagnetic microparticles (MMP) which are precoated with the carrier reagent DBCO-BSA and provide a preactivated surface for the subsequent covalent coupling of biologically active molecules by biorthogonal cycloaddition.

Paramagnetic nanoparticles (PMC-130, Kisker GmbH) were suspended in a concentration of 5.6 mg/ml in 10 mM Na-morpholinoethanesulfonic acid buffer (MES) pH 5.9; 12.5 mg/ml of N-hydroxysuccinimide and 25 mg/ml of N-ethyl-N'-(3-dimethylaminopropyl)carbodiimide hydrochloride were added thereto and the whole was incubated for 20 minutes at room temperature. The reaction mixture was then adjusted to pH 3.0 with 100 mM HCl. The nanoparticles were pelleted by means of a magnet, washed in 150 mM NaCl and then resuspended at a concentration of 5.6 mg/ml in 150 mM NaCl. For coupling of a BSA coating, 1% BSA in 25 mM HEPES buffer pH 7.98 was added to 1 ml of the activated nanoparticle suspension, and the whole was incubated for 20 hours at 4° C. The reaction was quenched by addition of 15 μl of 2 M ethanolamine pH 8.0. After incubation for 1 hour at room temperature, the BSA-coated nanoparticles were washed in 25 mM HEPES, 150 mM NaCl, pH 8.0 and resuspended in 20 ml of 25 mM HEPES, 150 mM NaCl, 20% DMSO, 0.05 mg/ml dibenzylcyclooctyne-PEG5 N-hydroxysuccinimide and incubated for 3 hours at room temperature. The DBCO-modified BSA nanoparticles were washed in 20 mM Na-HEPES, 1% BSA, pH 8.0 and stored at 4° C. at a particle concentration of 10 mg/ml in 20 mM Na-HEPES, 1% BSA, 0.05% Proclin, pH 8.0 until use.

Example 4: Production of Azide-Modified Proteinase-3

8-Azido-3,6-dioxaoctanoic acid N-hydroxysuccinimide ester was produced by a known method (George W. Anderson, Joan E. Zimmermann, Francis M. Callahan, J. Am. Chem. Soc., 1964, 86 (9), pp. 1839-1842). Proteinase-3 was dissolved in a concentration of 1 mg/ml in 50 mM HEPES, pH 8.0, 500 mM NaCl, and 10 μl/ml of an 8-azido-3,6-dioxaoctanoic acid N-hydroxysuccinimide ester stock solution (10 mg/ml in DMSO) were added thereto. The reaction mixture was incubated for 60 minutes at 37° C. Excess reagents and low molecular weight reaction products were removed by dialysis against 50 mM Na-HEPES, pH 8.0, 500 mM NaCl. The azide-modified proteinase-3 was stored at 20° C. until further use.

Example 5: Production of Azide-Modified Myeloperoxidase

Myeloperoxidase was dissolved in a concentration of 1 mg/ml in 50 mM Na-HEPES, pH 8.0, 500 mM NaCl, and 10 μl/ml of an 8-azido-3,6-dioxaoctanoic acid N-hydroxysuccinimide ester stock solution (10 mg/ml in DMSO) were added thereto. The reaction mixture was incubated for 60 minutes at 37° C., and then 0.1 μl/ml of 10% $H_2O_2$ and 0.1 μl/ml of 10% $NaN_3$ were added thereto and the whole was incubated for a further 60 minutes at 37° C. Excess reagents and low molecular weight reaction products were removed by dialysis against 50 mM Na-HEPES, pH 8.0, 500 mM NaCl. The azide-modified myeloperoxidase was stored at −20° C. until further use.

Example 6: Production of Microplates Coated with Proteinase-3, and Determination of PR3 Autoantibodies The following example describes the production of microplates coated with proteinase-3 (PR3) as an antigen surface for the detection of PR3 autoantibodies in human serum.

The azide-modified proteinase-3 produced according to Example 4 was diluted in a concentration of 0.5 μg/ml in blocking buffer (1×PBS, 0.5% BSA, 1% lactose, 5 mM EDTA) and pipetted in 100 μl aliquots into the wells of a microplate, produced according to Example 2, coated with DBCO-BSA carrier reagent. After incubation for 16 hours at 22° C., the wells were emptied, filled with 100 μl/well of the blocking solution and incubated for 1 hour at room temperature. A specific covalent coupling of the azide-modified proteinase-3 to the microplate precoated with DBCO-BSA carrier reagent thereby took place by biorthogonal cycloaddition. The plates were then emptied and dried for 2 hours at 37° C. The dried plates with a PR3 coating were stored at 4° C. in the presence of a silica gel desiccant until further use.

In order to test the suitability of the PR3 coating for detecting PR3 autoantibodies in human serum, a human anti-PR3 serum was diluted in sample buffer of a PR3 assay (ORG 518, ORGENTEC GmbH) in a serial dilution with dilution stages 1:50, 1:100, 1:200, 1:400, 1:1000, 1:2000. 100 μl of serum-free sample buffer and of each of the serum dilutions were pipetted into microplate wells coated with DBCO-BSA-PR3 or into antigen-free DBCO-BSA wells, and incubation was carried out for 30 minutes at 20-25° C. The microplates were washed and the binding of human PR3 autoantibodies was determined by means of an anti-human IgG peroxidase labelled secondary antibody and a tetramethylbenzidine (TMB) colour reaction by measuring the optical density at 450 nm.

Figure 1:
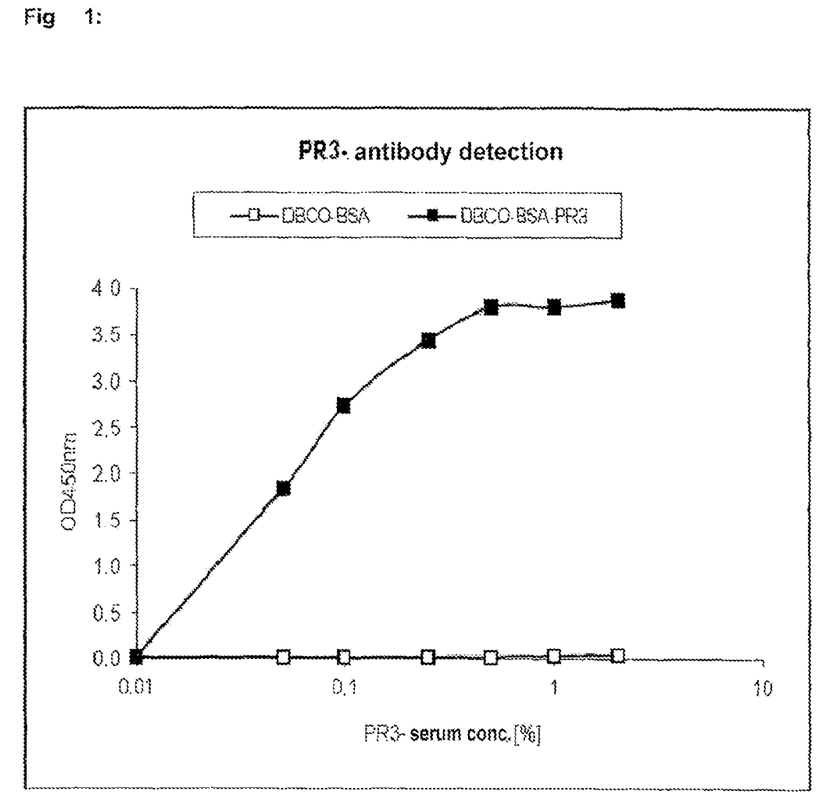
FIG. 1:
Determination of PR3 autoantibodies in human serum on microplates coated with DBCO-BSA-PR3. Dilutions of a human serum with PR3 autoantibodies in the indicated concentrations were tested in microplate wells coated with DBCO-BSA-PR3 and, for comparison, in microplate wells coated with antigen-free DBCO-BSA. The binding of PR3 autoantibodies to the well surface was thereby determined by means of a peroxidase-labelled anti-human IgG antibody and a TMB colour reaction by measuring the optical density at 450 nm.

As is shown in FIG. 1, PR3 autoantibodies could be specifically detected even at a 0.05% concentration (1:2000 dilution) of the test serum. The comparison of the reaction level of the serum dilution stages in the binding to microplates coated with PR3-DBCO-BSA or DBCO-BSA shows that, in the concentration range of 0-2% serum, PR3 autoantibodies were detected with high sensitivity and specificity, while only a low background signal occurred on the antigen-free DBCO-BSA carrier coating.

Example 7: Production of Microplate Surfaces Coated with Myeloperoxidase, and Determination of MPO Autoantibodies The following example describes the production of microplates coated with myeloperoxidase (MPO) as an antigen surface for the detection of MPO autoantibodies.

The azide-modified myeloperoxidase produced according to Example 5 was diluted in a concentration of 0.5 µg/ml in blocking buffer (1×PBS, 0.5% BSA, 1% lactose, 5 mM EDTA) and pipetted in 100 µl aliquots into the wells of a microplate, produced according to Example 2, coated with DBCO-BSA carrier reagent. After incubation for 16 hours at 22° C., the wells were emptied, filled with 100 µl/well of the blocking buffer and incubated for 1 hour at room temperature. The plates were then emptied and dried for 2 hours at 37° C. The dried plates with an MPO coating were stored at 4° C. in the presence of a silica gel desiccant until further use.

In order to test the suitability of the MPO coating for detecting MPO autoantibodies in human serum, a human anti-MPO serum was diluted in sample buffer of an MPO assay (ORG 519, ORGENTEC GmbH) in a serial dilution with dilution stages 1:50, 1:100, 1:200, 1:400, 1:1000, 1:2000. 100 µl of serum-free sample buffer and of each of the serum dilutions were pipetted into microplate wells coated with DBCO-BSA-MPO or into antigen-free DBCO-BSA wells, and incubation was carried out for 30 minutes at 20-25° C. The microplates were washed and the binding of human MPO autoantibodies was determined by means of an anti-human IgG peroxidase labelled secondary antibody and a tetramethylbenzidine (TMB) colour reaction by measuring the optical density at 450 nm.

Figure 2:
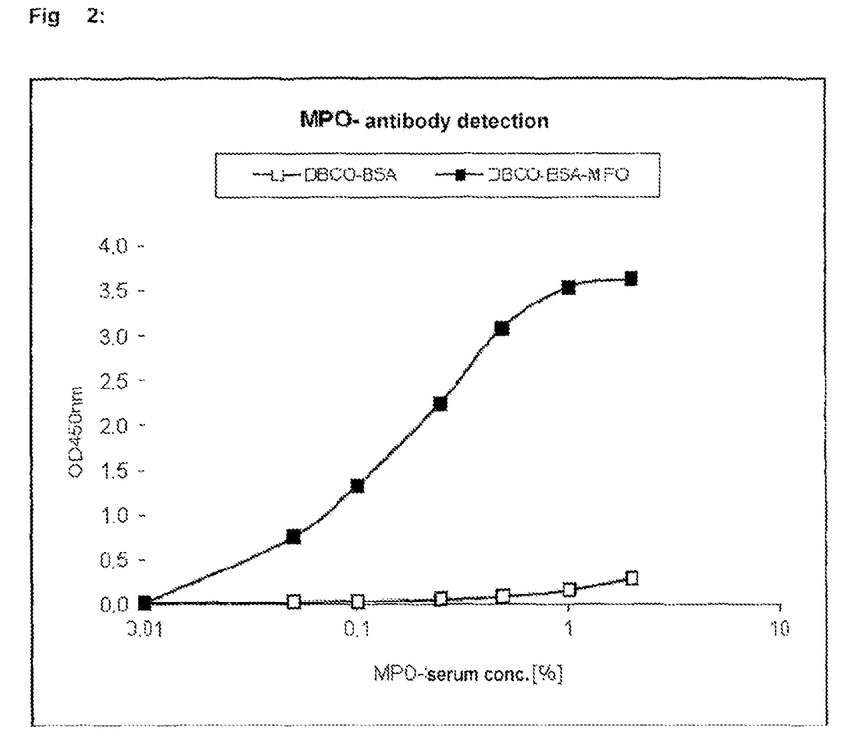
FIG. 2:
Determination of MPO autoantibodies in human serum on microplates coated with DBCO-BSA-MPO. Dilutions of a human serum with MPO autoantibodies in the indicated concentrations were tested in microplate wells coated with DBCO-BSA-MPO and, for comparison, in microplate wells coated with antigen-free DBCO-BSA. The binding of MPO autoantibodies to the well surface was thereby determined by means of a peroxidase-labelled anti-human IgG antibody and a TMB colour reaction by measuring the optical density at 450 nm.

As is shown in FIG. 2, MPO autoantibodies could be specifically detected even at a 0.05% concentration (1:2000 dilution) of the test serum. The comparison of the reaction level of the serum dilution stages in the binding to microplates coated with MPO-DBCO-BSA or DBCO-BSA shows that, in the concentration range of 0-2% serum, MPO autoantibodies were detected with high sensitivity and specificity, while only a low background signal occurred on the antigen-free DBCO-BSA carrier coating.

Example 8: Production of Paramagnetic Nanoparticles Coated with Proteinase-3, and Determination of PR3 Autoantibodies The following example describes the production of paramagnetic nanoparticles coated with proteinase-3 (PR3) and the determination of PR3 autoantibodies.

Azide-modified proteinase-3 according to Example 4 was diluted in a concentration of 40 µg/ml in blocking buffer (20 mM Na-HEPES, pH 8.0, 1% BSA) and incubated for 16 hours at 22° C. in the presence of 2% nanoparticles, produced according to Example 3, coated with DBCO-BSA carrier reagent. The paramagnetic nanoparticles were washed in 1.5 ml of blocking buffer and stored at 4° C. at a particle concentration of 2% in 20 mM Na-HEPES, pH 8.0, 1% BSA, 0.05% Proclin until use.

In order to test the suitability of the PR3-coated nanoparticles for detecting PR3 autoantibodies in human serum, a human anti-PR3 serum was diluted in sample buffer of a PR3 assay (ORG 518, ORGENTEC GmbH) in a serial dilution with dilution stages 1:50, 1:100, 1:200, 1:400, 1:800, 1:1600, 1:3200. 5 µl of the PR3-coated nanoparticles were added to 100 µl of serum-free sample buffer and of each of the serum dilutions, and incubation was carried out for 30 minutes at 20-25° C. The particles were pelleted in the magnetic field and washed. The binding of human PR3 autoantibodies was determined by means of an anti-human IgG peroxidase labelled secondary antibody and a tetramethylbenzidine (TMB) colour reaction by measuring the optical density at 450 nm.

Figure 3:
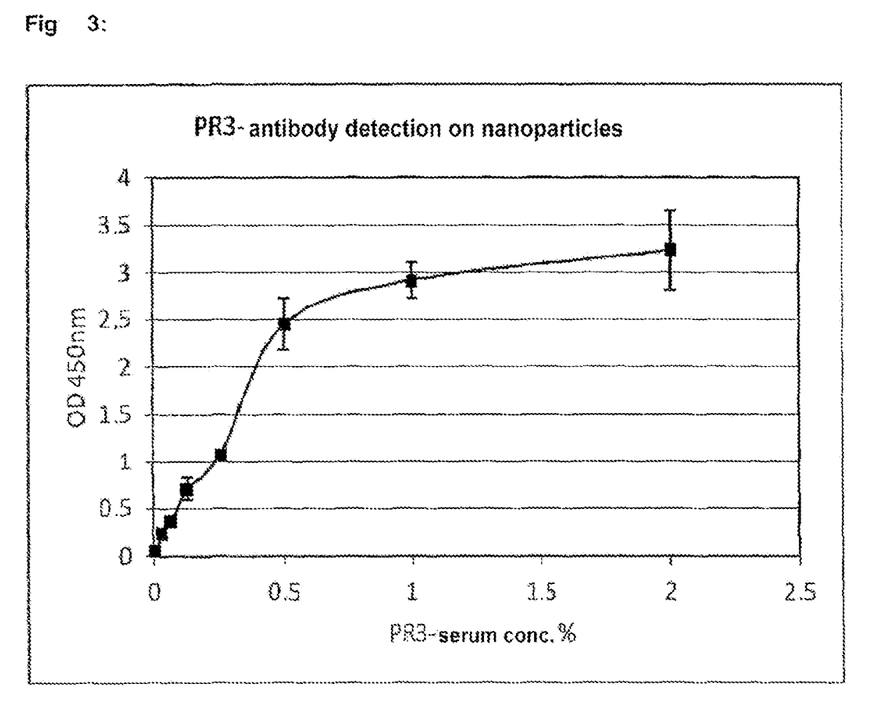
FIG. 3:
Determination of PR3 autoantibodies in human serum on paramagnetic nanoparticles coated with DBCO-BSA-PR3. Paramagnetic nanoparticles coated with -BSA-PR3 were added to dilutions of a human serum with PR3 autoantibodies in the indicated concentrations. The binding of PR3 autoantibodies to the nanoparticles was thereby determined by means of a peroxidase-labelled anti-human IgG antibody and a TMB colour reaction by measuring the optical density at 450 nm.

As is shown in FIG. 3, PR3 autoantibodies could be specifically detected even at a 0.03% concentration (1:3200 dilution) of the test serum.

Example 9: Production of Bovine Serum Albumin Modified with 8-Azido-3,6-Dioxaoctanoic Acid as Carrier Reagent The following example describes the production of bovine serum albumin modified with 8-azido-3,6-dioxaoctanoic acid as a reactive carrier reagent for the coating of surfaces. Bovine serum albumin was dissolved in a concentration of 20 mg/ml in 20 mM HEPES, pH 7.5, 120 mM NaCl and reacted for 60 minutes at 22° C. with a 30-times molar excess of 8-azido-3,6-dioxaoctanoic acid N-hydroxysuccinimide ester (IRIS Biotech). Excess reagent and low molecular weight reaction products were removed by repeated dialysis against 20 mM HEPES, pH 7.5, 120 mM NaCl. The reaction product, referred to as azide-BSA, was stored frozen at −20° C. until use.

Example 10: Production of Nanoparticles Coated with Azide-BSA Carrier Reagent The following example describes the production of paramagnetic microparticles (MMP) which are precoated with the carrier reagent azide-BSA.

Paramagnetic nanoparticles (EM1 100/40, ESTAPOR) were suspended in a concentration of 3.3 mg/ml in 10 mM Na-morpholinoethanesulfonic acid buffer (MES) pH 5.7; 0.70 mg/ml of azide-BSA and 0.58 mg/ml of N-ethyl-N'-(3-dimethylaminopropyl)carbodiimide hydrochloride were added thereto, and the whole was incubated for 180 minutes at room temperature. The nanoparticles were pelleted by means of a magnet and washed in 25 mM HEPES, 150 mM NaCl, pH 8.0. The azido-modified BSA nanoparticles were washed in 20 mM Na-HEPES, 1% BSA, pH 8.0 and stored at 4° C. at a particle concentration of 10 mg/ml in 20 mM Na-HEPES, 1% BSA, 0.05% Proclin, pH 8.0 until use.

Example 11: Production of DBCO-Modified β2-Glycoprotein

Human β2-glycoprotein was dissolved in a concentration of 2.5 mg/ml in 20 mM Na-MES, pH 5.5, 120 mM NaCl, and 9 µl/ml of dibenzylcyclooctyne-PEG5 N-hydroxysuccinimide (10 mg/ml in DMSO) were added thereto. The reaction mixture was incubated for 16 hours at 4° C. Excess reagents and low molecular weight reaction products were removed by dialysis against 20 mM Na-HEPES, pH 8.0, 120 mM NaCl. The DBCO-modified β2-glycoprotein was stored at −20° C. until further use.

Example 12: Production of DBCO-Modified Cardiolipin 5 mg of meta-chloroperbenzoic acid were added to 10 ml of a 0.5% cardiolipin solution in dichloromethane, and the whole was incubated for 24 hours at 4° C. After addition of 10 ml of dichloromethane, the mixture was extracted 2× with 10 ml of 10% sodium carbonate each time. The dichloromethane fraction was dried over $MgSO_4$; 0.2 ml of 1,2-ethylenediamine was added thereto, and the whole was incubated for 16 hours at room temperature. The reaction mixture was extracted 3× with 10 ml of 10% citric acid each time. The organic phase contains amino-cardiolipin and was concentrated in vacuo to give a colourless oil. Amino-cardiolipin was dissolved in 10.0 ml of dichloromethane; 2 μl of triethylamine and 6 mg of dibenzylcyclooctyne-PEG5 N-hydroxysuccinimide were added thereto and the whole was reacted for 16 hours at room temperature. The solvent was evaporated off under reduced pressure and the residue was purified by silica gel column chromatography. 50.0 mg of DBCO-(PEG5)-cardiolipin were obtained in the form of a colourless wax.

Example 13: Production of Paramagnetic Nanoparticles Coated with Cardiolipin/β2-Glycoprotein, and Determination of Cardiolipin/β2-Glycoprotein Autoantibodies Nanoparticles coated with azide-BSA carrier reagent according to Example 10 were diluted as a 2% suspension in blocking buffer (20 mM Na-HEPES, pH 8.0, 120 mM NaCl, 1% BSA); DBCO-β2-glycoprotein (80 μg/ml) or a mixture of DBCO-β2-glycoprotein (80 μg/ml) and DBCO-cardiolipin (40 μg/ml) were added thereto in reaction batches, and incubation was carried out for 2 hours at 22° C. The paramagnetic nanoparticles covalently loaded with β2-glycoprotein or with a mixture of β2-glycoprotein and cardiolipin were washed in blocking buffer and stored at 4° C. at a particle concentration of 2% in 20 mM Na-HEPES, pH 8.0, 1% BSA, 0.05% Proclin.

Figure 4:
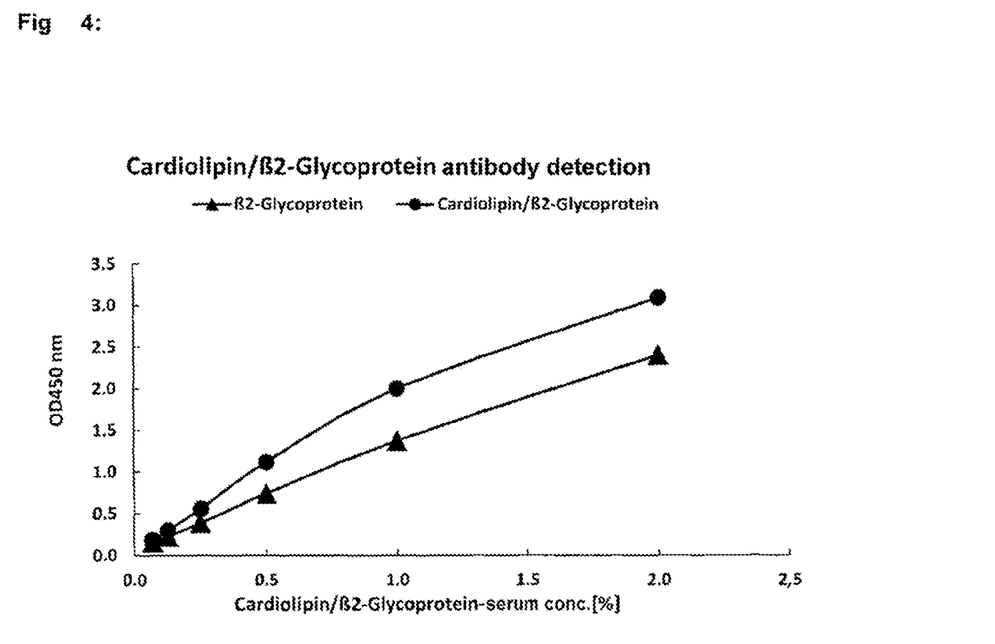
FIG. 4:
Determination of cardiolipin/β2-glycoprotein autoantibodies in human serum on paramagnetic nanoparticles coated with azide-BSA-β2-glycoprotein or with azide-BSA-cardiolipin-β2-glycoprotein. Coated paramagnetic nanoparticles were added to dilutions of a human serum with cardiolipin/β2-glycoprotein autoantibodies in the indicated concentrations. The binding of cardiolipin/β2-glycoprotein autoantibodies to the nanoparticles was thereby determined by means of a peroxidase-labelled anti-human IgG antibody and a TMB colour reaction by measuring the optical density at 450 nm.

In order to test the suitability of the cardiolipin/β2-glycoprotein nanoparticles for detecting cardiolipin/β2-glycoprotein autoantibodies in human serum, a human anti-cardiolipin/β2-glycoprotein serum was diluted in sample buffer of a cardiolipin/β2-glycoprotein assay (ORG 515, ORGENTEC GmbH) in a serial dilution with dilution stages 1:100, 1:200, 1:400, 1:800, 1:1600, 1:3200. 5 μl of the nanoparticles coated with cardiolipin/β2-glycoprotein were added to 100 μl of serum-free sample buffer and of each of the serum dilutions, and incubation was carried out for 30 minutes at 20-25° C. The particles were pelleted in the magnetic field and washed. The binding of human cardiolipin/β2-glycoprotein autoantibodies was determined by means of an anti-human IgG peroxidase labelled secondary antibody and a tetramethylbenzidine (TMB) colour reaction by measuring the optical density at 450 nm. As is shown in FIG. 4, cardiolipin/β2-glycoprotein autoantibodies could thereby be specifically detected. In the case of the nanoparticles coated with both antigens, cardiolipin and β2-glycoprotein, an additive effect of the reactivity is visible.

The invention claimed is:

1. A method for binding biologically active molecules to a surface of a substrate, comprising the steps of:
   (i) providing a carrier molecule comprising at least one alkyne or azide click functional group, wherein the carrier molecule is human serum albumin or bovine serum albumin, wherein said carrier molecule comprising said at least one alkyne or azide click functional group is obtained by treating the carrier molecule with a molar excess of dibenzylcyclooctyne-PEG5 N-hydroxysuccinimide ester or a molar excess of 8-azido-3,6-dioxaoctanoic acid N-hydroxysuccinimide ester such that at least some of the dibenzylcyclooctyne-PEG5 N-hydroxysuccinimide ester or 8-azido-3,6-dioxaoctanoic acid N-hydroxysuccinimide ester are covalently bound to the carrier molecule via the N-hydroxysuccinimide ester group,
   (ii) binding the carrier molecule comprising the at least one alkyne or azide click functional group to a surface of a substrate, wherein the carrier molecule is adsorptively bound to the surface of the substrate,
   (iii) binding a biologically active molecule comprising at least one click functional group that is reactive towards the at least one alkyne or azide click functional group of the carrier molecule, to the surface bound carrier molecule comprising the at least one alkyne or azide click functional group by a cycloaddition reaction between the mutually reactive click functional groups, wherein the substrate comprises plastic material selected from the group consisting of polystyrene, polypropylene, polyethylene, polyamide, polymethacrylate, polycarbonate, polyacrylate, and copolymers of polystyrene; glass; ceramics; latex; metal; or carbon.

2. Method according to claim 1, wherein the substrate is in the form of a plate, in particular a microplate, or in the form of microparticles or nanoparticles.

3. Method according to claim 1, wherein the biologically active molecule is selected from the group consisting of proteins, enzymes, antibodies, nucleic acids and low molecular weight ligands of proteins, enzymes, antibodies or nucleic acids.

4. The method according to claim 1, wherein, said metal is gold.

5. The method according to claim 1, wherein said substrate is polystyrene.

6. An article, comprising
(i) a substrate having a surface,
(ii) a carrier molecule comprising at least one alkyne or azide click functional group, wherein the carrier molecule is human serum albumin or bovine serum albumin, wherein said carrier molecule comprising said at least one alkyne or azide click functional group is obtained by treating the carrier molecule with a molar excess of dibenzylcyclooctyne-PEG5 N-hydroxysuccinimide ester or a molar excess of 8-azido-3,6-dioxaoctanoic acid N-hydroxysuccinimide ester such that at least some of the dibenzylcyclooctyne-PEG5 N-hydroxysuccinimide ester or 8-azido-3,6-dioxaoctanoic acid N-hydroxysuccinimide ester are covalently bound to the carrier molecule via the N-hydroxysuccinimide ester group,
wherein the carrier molecule comprising said at least one alkyne or azide click functional group is adsorptively bound to the surface of the substrate and wherein the substrate comprises plastic material selected from the group consisting of polystyrene, polypropylene, polyethylene, polyamide, polymethacrylate, polycarbonate, polyacrylate and copolymers of polystyrene; glass; ceramics; latex; metal; and carbon, and
(iii) a biologically active molecule comprising at least one alkyne or azide click functional group that is reactive to the at least one alkyne or azide click functional group of the carrier molecule is covalently bound to the surface bound carrier molecule via a cycloaddition reaction between the mutually reactive click functional groups.

* * * * *